US00PP27575P3

(12) United States Plant Patent
Olesen

(10) Patent No.: US PP27,575 P3
(45) Date of Patent: Jan. 24, 2017

(54) CLIMBING ROSE PLANT NAMED 'POULCY033'

(50) Latin Name: ***Rosa* hybrid**
Varietal Denomination: Poulcy033

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 182 days.

(21) Appl. No.: 14/121,263

(22) Filed: Aug. 15, 2014

(65) Prior Publication Data

US 2016/0050801 P1 Feb. 18, 2016

(51) Int. Cl.
*A01H 5/02* (2006.01)

(52) U.S. Cl.
USPC ..... Plt./109

(58) Field of Classification Search
USPC ..... Plt./109, 114
See application file for complete search history.

*Primary Examiner* — Keith Robinson

(57) ABSTRACT

A new garden rose plant of the Climbing class which has abundant, mauve flowers and attractive foliage. This new and distinct variety has shown to be uniform and stable in the resulting generations from asexual propagation.

2 Drawing Sheets

Botanical designation: *Rosa* hybrid.
Variety denomination: 'Poulcy033'.

SUMMARY OF THE INVENTION

The present invention constitutes a new and distinct variety of garden rose plant which originated from a controlled crossing between the female seed parent, an unnamed, non-patented, seedling, and the male pollen parent, also an unnamed, non-patented, seedling.

The two parents were crossed during the summer of 2006 and the resulting seeds were planted in a controlled environment in Fredensborg, Denmark. The new variety, named 'Poulcy033', originated as a single seedling from the stated cross.

The new variety may be distinguished from its male pollen parent and female seed parent by the following characteristics. The female seed parent is a compact miniature rose, compared with the new plant which is a climbing rose. The male pollen parent has dark red flowers, while the new variety has mauve flowers.

The objective of the hybridization of this rose variety was to create a new and distinct variety for garden use with unique qualities, such as:

1. Uniform and abundant mauve flowers;
2. Vigorous, but compact growth when propagated both as a budded rose and on its own roots;
3. Exceptional disease resistance.
4. Reduced apical dominance in flowering with climbing rose characteristics. The new variety consistently produces flowers evenly from the lower branches to the top of the plant.

This combination of qualities is not present in previously available commercial cultivars of this type, known to the inventor, and distinguish 'Poulcy033' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulcy033' was selected in the spring of 2007 by the inventor as a single plant from the progeny of the aforementioned hybridization.

Asexual reproduction of 'Poulcy033' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poulcy033' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy033'.

Specifically illustrated in FIG. 1 of the drawings are flowers at various stages of development, and flowers in parts.

DETAILED DESCRIPTION OF THE VARIETY

Figure 1:
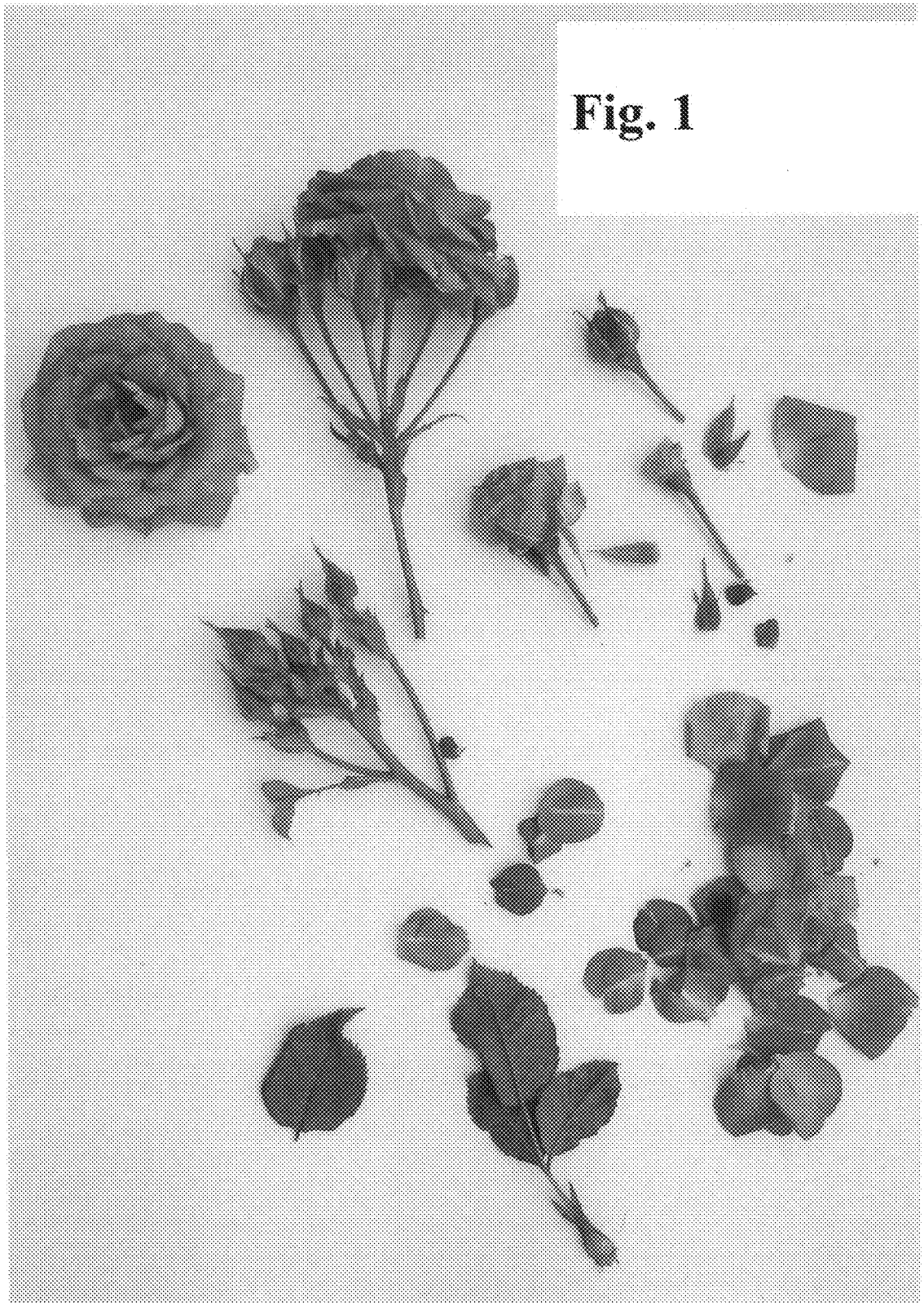
Figure 2:
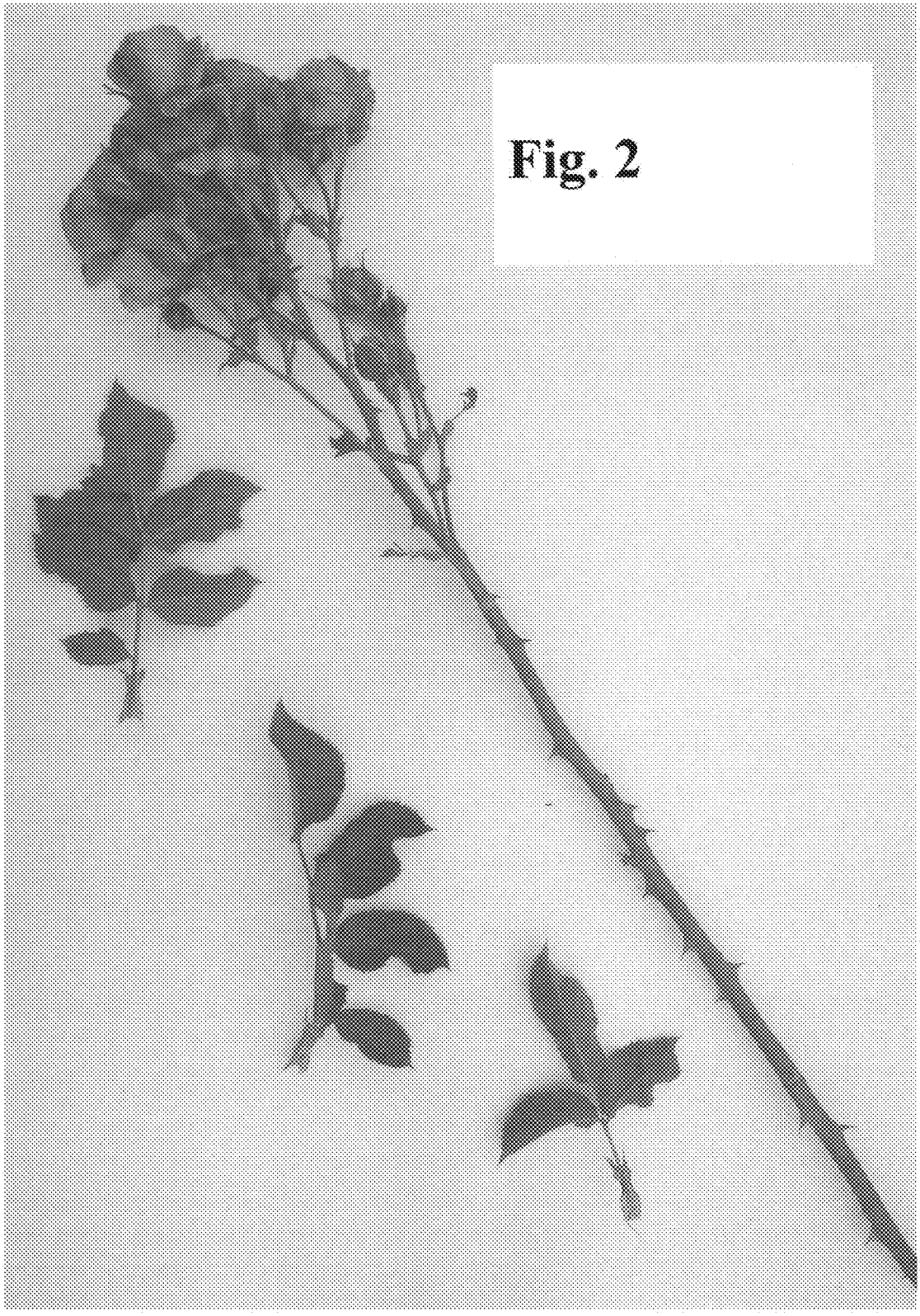
FIG. 2 is a flowering branch with leaves, and stems. Plants shown are 2 years of age.

The following is a description of 'Poulcy033', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulren013', U.S. Plant Pat. No. 16,541 are compared to 'Poulcy033' in Chart 1.

CHART 1

| | 'Poulcy033' | 'Poulren013' |
|---|---|---|
| Petal Count | 65 petals total, 7 to 9 of which are petaloids | 50 |
| Flower Diameter | 65 mm | 85 mm |
| General Tonality of Flower Color | Purple Group N78B | Red-Purple Group 61D towards flower center becoming Red-Purple Group 65B at the outer petals |

FLOWER AND FLOWER BUD

Blooming habit: Continuous.

Flower bud:

*Size.*—Upon opening, 20 mm in length from base of receptacle to end of bud. Bud diameter is 15 mm.

*Bud form.*—Ovoid.

*Bud color.*—As sepals divide petals are Red-Purple Group 68A.

*Sepal inner surface.*—Color: Green Group 138A. Surface: Smooth and pubescent.

*Sepal outer surface.*—Color: Yellow-Green Group 144A with light intonations of Greyed-Orange Group 175A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—20 mm long by 7 mm wide.

*Receptacle.*—Texture: Smooth. Size: 8 mm in height by 8 mm wide. Color: Yellow-Green Group 144A with light intonations of Greyed-Orange Group 175A. Shape: Campanulate.

*Pedicel.*—Surface: Somewhat rough with stipitate glands. Length: 40 to 45 mm. Diameter: 2 mm on average. Color: Yellow-Green Group 144B with intonations of Greyed-Orange Group 175B. Strength: Moderate.

*Peduncle.*—Length: 5 to 20 cm. Diameter: 5 mm. Color: Yellow-Green Group 144A. Texture: Smooth.

Flower bud development: Flower buds are borne in clusters of 11 flower buds per stem on average, resembling a panicle.

Flower bloom:

*Fragrance.*—Strong, perfume with hints of cloves.

*Duration.*—The blooms have a duration on the plant of approximately 7 to 10 days. Petals fall cleanly away from plant after flowers have fully matured.

*Size.*—Flower diameter is 65 mm when open. Flower depth is 25 mm.

*Flower shape.*—Double. General shape is a rosette with many overlapping petals of various sizes.

*Shape of flower, side view.*—The upper portion is rounded. The lower portion is concave.

Petalage: Under normal conditions, flowers have 65 petals total, 7 to 9 of which are petaloids.

General tonality of flower: Open flowers are Purple Group N78B.

Petal color:

*Upon opening, inner and outer petals.*—Upper surface: Red-Purple Group N74A. Lower surface: Red-Purple Group 70D with splashes of Red-Purple Group 69A and streaks of Red-Purple Group 69D. Petal spot: Yellow Group 3C to White Group 155A, approximately 3 to 5 mm in length.

*After opening, inner and outer petals.*—Upper surface: Red-Purple Group N74C with intonations of Red-Purple Group 70A. Lower surface: Purple Group 76A with streaks of Purple Group 76C.

Petal characteristics:

*Petal reflex.*—Somewhat reflexed.

*Margin.*—Entire and uniform. Occasionally there is a cleft at the center of the margins. Weak undulations.

*Shape.*—Generally elliptical. Apex shape: Rounded. Base shape: Acute.

*Size.*—37 mm (l) 32 mm (w).

*Texture.*—Smooth on both upper and lower surfaces.

*Thickness.*—Average.

Petaloids:

*Size.*—22 mm (l) by 10 mm (w).

*Quantity.*—About 7 to 9.

*Shape.*—Heart shaped.

*Color.*—The upper surface is Red-Purple Group N74C with intonations of Red-Purple Group 70A. The under surface is Purple Group 76A with streaks of Purple Group 76C and White Group N155A.

Reproductive organs:

*Pollen.*—None observed.

*Anthers.*—Size: 2 mm in length. Color: Greyed-Orange Group 167A. Quantity: 30 on average.

*Filaments.*—Color: Yellow Group 10A. Length: 7mm.

*Pistils.*—Length: 5 mm. Quantity: 20 on average.

*Stigmas.*—Color: Greyed-White Group 157A.

*Styles.*—Color: White Group 155A. Location of stigmas: Inferior in location relative to the length of the filaments and the height of the anthers.

*Hips.*—None Observed.

PLANT

Plant growth: Climbing, upright. Plants are 90 cm in height, and 70 cm wide.

Stems:

*Color.*—Juvenile growth: Yellow-Green Group 144A. Mature growth: Yellow-Green Group 146B.

*Length.*—On average, canes are 40 cm from the base of the plant to the flowering portion.

*Diameter.*—10 mm.

*Internodes.*—On mature canes, there is an average distance of 40 to 50 mm between nodes.

*Surface texture.*—Young wood: Smooth. Older wood: Smooth.

Long prickles:

*Incidence.*—11 prickles per 10 cm of stem.

*Size.*—Average length of prickles on mature stems is 11 mm.

*Shape.*—Upper portion is linear. Lower portion is concave.

*Color.*—Juvenile prickles: Greyed-Red Group 182A. Mature prickles: Greyed-Orange Group 167D.

Plant foliage:

*Compound leaf.*—150 mm (l)×110 (w).

*Quantity.*—2 leaves per 10 cm of stem on average.

*Color of juvenile foliage.*—Upper side: Yellow-Green Group 144A. Margins are Greyed-Purple Group 183C. Lower side: Yellow-Green Group 144B.

*Color of mature foliage*.—Upper side: Yellow-Green Group 146A. Lower side: Yellow-Green Group 146B.

Plant leaves and leaflets:

*Stipules*.—Size: 25 mm in length. Quantity: 2 per compound leaf. Shape: Linear, slightly broad based with outward extending apices. Margins: Finely serrated. Color: Yellow-Green Group 144A.

*Petiole*.—Length: 20 mm. Diameter: 1-2 mm.

*Upper surface*.—Color: Yellow-Green Group 144A.

*Lower surface*.—Color: Yellow-Green Group 144B.

*Rachis*.—Length: 70 mm. Upper surface: Color: Yellow-Green Group 144A.

*Lower surface*.—Color: Yellow-Green Group 144B.

*Leaflet*.—Quantity: Normal number of leaflets leaves in middle of the stem is 5 leaflets. Margins: Serrated. Size: Average size of the terminal leaflet on normal leaves is 52 mm in length by 35 mm wide. Shape: Generally elliptical. Base: Rounded. Apex: Acute. Cuspidate. Texture: Smooth on both upper and lower surfaces. Thickness: Average. Arrangement: Odd pinnate. Venation: Reticulate. Glossiness: Glossy. Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticultural Society heat zone 7.

The invention claimed is:

1. A new and distinct variety of rose plant of the Climbing rose class named 'Poulcy033', substantially as illustrated and described herein, due to its abundant mauve flowers, disease resistance, and extended period of bloom.

* * * * *